(12) United States Patent
Gupta et al.

(10) Patent No.: US 7,487,684 B2
(45) Date of Patent: Feb. 10, 2009

(54) GLASS-MODIFIED STRESS WAVES FOR SEPARATION OF ULTRA THIN FILMS AND NANOELECTRONICS DEVICE FABRICATION

(75) Inventors: Vijay Gupta, Sherman Oaks, CA (US); Vassili A Kireev, Sunnyvale, CA (US)

(73) Assignee: The Regents of the University of California, Oakland, CA (US)

( * ) Notice: Subject to any disclaimer, the term of this patent is extended or adjusted under 35 U.S.C. 154(b) by 40 days.

(21) Appl. No.: 11/504,981

(22) Filed: Aug. 15, 2006

(65) Prior Publication Data

US 2007/0039395 A1    Feb. 22, 2007

Related U.S. Application Data

(63) Continuation of application No. PCT/US2005/007304, filed on Mar. 7, 2005.

(60) Provisional application No. 60/550,803, filed on Mar. 5, 2004.

(51) Int. Cl.
*G01L 1/24* (2006.01)

(52) U.S. Cl. ........................................................ 73/800

(58) Field of Classification Search .................. 73/777, 73/862.49; 356/35.5
See application file for complete search history.

(56) References Cited

U.S. PATENT DOCUMENTS

| | | | | |
|---|---|---|---|---|
| 4,353,649 A | * | 10/1982 | Kishii | 356/33 |
| 4,722,600 A | * | 2/1988 | Chiang | 356/32 |
| 5,199,304 A | * | 4/1993 | Ferguson | 73/800 |
| 5,438,402 A | | 8/1995 | Gupta | |
| 5,920,017 A | * | 7/1999 | Pechersky | 73/762 |
| 6,219,139 B1 | * | 4/2001 | Lesniak | 356/366 |
| 6,327,030 B1 | * | 12/2001 | Ifju et al. | 356/32 |
| 6,466,308 B1 | * | 10/2002 | Jaing et al. | 356/35.5 |

* cited by examiner

*Primary Examiner*—Edward Lefkowitz
*Assistant Examiner*—Octavia Davis
(74) *Attorney, Agent, or Firm*—John P. O'Banion

(57) ABSTRACT

A device for generating a tensile force between a substrate and a coating, wherein the substrate has a thickness defined by a first side and a second side in a first axis, and the coating is applied to the first side of the substrate such that the coating and substrate are axially spaced along the first axis in intimate facing contact with each other to form a coating/substrate interface. The apparatus has a glass element disposed on the second side of the substrate and axially spaced along the first axis. The glass element is configured to propagate a stress wave to the coating/substrate interface to generate a tensile force between the substrate and the coating.

36 Claims, 12 Drawing Sheets

GLASS-MODIFIED STRESS WAVES FOR SEPARATION OF ULTRA THIN FILMS AND NANOELECTRONICS DEVICE FABRICATION

CROSS-REFERENCE TO RELATED APPLICATIONS

This application claims priority from, and is a 35 U.S.C. § 111(a) continuation of, co-pending PCT international application serial number PCT/US2005/007304, filed on Mar. 7, 2005, incorporated herein by reference in its entirety, which designates the U.S., which claims priority from U.S. provisional application Ser. No. 60/550,803 filed on Mar. 5, 2004, incorporated herein by reference in its entirety.

STATEMENT REGARDING FEDERALLY SPONSORED RESEARCH OR DEVELOPMENT

This invention was made with Government support under Grant No. DAAD19-00-1-0491 awarded by the Army Research Office. The Government has certain rights in this invention.

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND OF THE INVENTION

1. Field of the Invention

This invention pertains generally to the application of a coating onto fibers or flat substrates, and more particularly to an improved method and system for generating spallation of ultra thin films and measuring the interface tensile strength between a substrate and the thin film.

2. Description of Related Art

Films and coatings have widespread use in different industries. Examples include thermal barrier coatings for engines; tribological coatings in cutting tools, seals, and joints; polymeric layers in paint assemblies; fiber coatings in composites; electrical, magnetic and optical multilayers in electronic devices; metal and ceramic films in MEMS-based mechanical and clinical devices, among others. In the field of composite materials, the interface between a thin coating and a fiber is considered for deflecting impinging matrix cracks. In the field of tribology, interfaces between various types of functional coatings, e.g., magnetic, conducting, optical, or electrical, protective coatings, e.g., thermal barrier, corrosion, or wear resistant, or decorative coatings and their underlying substrates are of interest.

In the foregoing various applications, the tensile strength of the interface is an important property that directly controls the interface decohesion process, and often controls the usefulness and reliability of the coating component. Adhesion of films is a prerequisite to carryout their intended functions. Thus, the central goal in all these applications is to avoid film delamination and coating failures by maximizing adhesion, and to predict long-term reliability of the coated components. Additionally, the measurement of the interface tensile strength is of importance for reliable performance of the coating in the above applications. These issues are usually addressed by seeking a fundamental understanding of the adhesion between different layers as a function of process (film deposition and surface variables) and service (moisture and temperature) variables.

These objectives are currently accomplished using adhesion metrology tools, such as the laser spallation technique commonly applied in the art. Typically, a high energy laser pulse is made to impinge upon a planar arrangement of a confining plate, a metallic layer, a substrate plate, and a coating combination. The laser pulse impinges on a thick metal film that is sandwiched between the back surface of a substrate of interest and a fused quartz confining plate that is transparent to the wavelength of the laser. Normally, gold or aluminum is used as the laser absorbing film. Absorption of the laser energy in the confined gold leads to a sudden expansion of the film which, due to the axial constraints of the assembly, leads to the generation of a compressive shock wave directed towards the test coating interface. A part of the compressive pulse is transmitted into the coating as the compression pulse strikes the interface. It is the reflection from the free surface of the coating of this compressive pulse into a tension pulse that leads to the removal of the coating, given a sufficiently high amplitude.

U.S. Pat. No. 5,438,402 provides significant improvement in the art to determine the tensile strength of planar interfaces down to 1 micrometer in thickness. However, ultra-thin layers with thickness below 0.5 micrometers are now the focus of research in the microelectronics industry for developing ultrahigh density devices using nanotechnology. In addition, adhesion at similar length scales will become important in the material optimization of MEMS-based mechanical and clinical devices when they are mass-produced. Therefore, there is a need to extend measurement capabilities to films below 0.5 µm in thickness.

Accordingly, an object of the present invention is to measure the tensile strength of interfaces between such very thin films.

Another object is to separate and lift thin film lines or their complete structures from semiconductor and engineering substrates using glass-modified stress waves, and catch them on desired substrates for reconstructing structures. This can lead to a faster way of fabricating MEMS and nano-scale devices by bypassing the currently used wet-etching techniques. At least some of these objectives will be met in the following invention.

BRIEF SUMMARY OF THE INVENTION

An aspect of the invention is an apparatus for generating a tensile stress between a substrate and a coating, wherein the substrate has a thickness defined by a first side and a second side in a first axis, and the coating is applied to the first side of the substrate such that the coating and substrate are axially spaced along the first axis in intimate facing contact with each other to form a coating/substrate interface. The apparatus has a glass element disposed on the second side of the substrate and axially spaced along the first axis. The glass element is configured to propagate a stress wave to the coating/substrate interface to generate a tensile force or stress between the substrate and the coating.

In a preferred mode of the present aspect, the tensile stress is configured to separate the coating from the substrate at the coating/substrate interface. Generally, the stress waves have a length ranging from approximately 5 nanoseconds to approximately 100 nanoseconds. Ideally, the stress waves comprise a rarefaction shock formation. The glass substrate is configured to allow separation of a coating having a thickness less than approximately 0.5 µm. However, the present invention may also be used on a variety of coatings with thickness greater than approximately 0.5 µm.

In one embodiment, the glass is configured to propagate the stress wave as a result of impingement by a Nd-Yag laser beam directed in the first axis. Typically, the glass element is bonded to the second side of the substrate. The glass element may comprise Pyrex, soda lime, quartz, borosilicate or similar material. The glass element may have any thickness, but preferably has a thickness ranging from approximately 0.1 mm to approximately 5 mm.

In some embodiments, the apparatus may further include a constraining element disposed adjacent to the glass element. In addition, an energy absorbing layer may be disposed between the constraining layer and the glass element.

Another aspect of the invention comprises a method for separating a coating from a substrate, the substrate having a first side and a second side transversely disposed in a first axis, where the coating is applied to the first side of the substrate such that the coating and substrate are axially spaced along the first axis in intimate facing contact to form a coating/substrate interface. The method comprises the steps of positioning a glass element along the first axis on the second side of the substrate, directing a laser pulse in the first axis at the glass element, propagating a stress wave through the glass element to the coating/substrate interface to generate a tensile stress between the substrate and the coating, and separating the coating from the substrate as a result of the stress wave-generated tensile stress.

In a preferred embodiment, the propagated stress wave has a length configured to separate a coating having a thickness less than approximately 0.5 µm.

In another embodiment, the method further includes positioning a glass element along the first axis comprises bonding the glass element to the second side of the substrate. In addition, a constraining element may be placed adjacent to a free side of the glass element. The method may further include coating an energy absorbing layer on the free side of the glass element between the constraining layer and the glass element such that directing a laser pulse in the first axis comprises directing the laser pulse the energy absorbing layer coated on the glass element.

In one mode of the present aspect, the stress generated by the stress wave at the coating/substrate interface exceeds approximately 1.0 GPa. In particular, the stress generated by the stress wave at the coating/substrate interface exceeds approximately 2.0 GPa.

In yet another aspect of the invention, an apparatus is disclosed for separating a nanostructure from a first substrate, the nanostructure attached to a front side of the first substrate. The apparatus comprises a glass element disposed on a back side of the first substrate opposite the nanostructure a laser source, a Nd-Yag laser, configured to direct a laser beam at the glass element. The glass element is configured to propagate a stress wave to the nanostructure as a result of impingement by the laser beam to generate a tensile stress between the nanostructure and the first substrate to separate the nanostructure from the first substrate.

In one mode of the current aspect, the apparatus further comprises a second substrate located opposite the front side of the first substrate where the second substrate is configured to receive the nanostructure once separated from the first substrate.

In a preferred embodiment, the apparatus further includes an adhesive layer disposed on the second substrate. The adhesive layer is generally configured to form a bond between the nanostructure and the second substrate. One or more spacers may further be included to separate the first substrate from the second substrate.

In a further aspect, an apparatus for transferring a silicon platform to a receiving substrate comprises a glass substrate disposed on a back side of the silicon platform, and a laser source configured to direct a laser beam at the glass element. The glass element is configured to generate a tensile stress between the silicon platform and the glass substrate as a result of impingement by the laser beam such that the tensile stress launches the silicon platform to the receiving substrate.

In one mode of the current aspect, an energy absorbing layer may be positioned adjacent the glass substrate opposite from the silicon platform, such that the energy absorbing layer and the glass substrate are configured to propagate a stress wave across the glass substrate to generate the tensile stress between the silicon platform and the glass substrate.

In another mode without an energy absorbing layer, the laser beam passes through the glass substrate to generate the tensile stress between the silicon platform and the glass substrate.

In many embodiments, the silicon platform comprises one or more circuits. The silicon platform may also comprise a thin Si film.

In another mode, the receiving substrate comprises a polymer. The receiving substrate may also be spun coated with a polymer film.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWINGS

The invention will be more fully understood by reference to the following drawings which are for illustrative purposes only.

DETAILED DESCRIPTION OF THE INVENTION

Referring more specifically to the drawings, for illustrative purposes the present invention is embodied in the apparatus generally shown in FIG. 4 through FIG. 6 and FIG. 7B through FIG. 13. It will be appreciated that the apparatus may vary as to configuration and as to details of the parts, and that the method may vary as to the specific steps and sequence, without departing from the basic concepts as disclosed herein.

The apparatus and methods of the current invention measure the tensile strength (adhesion) of very thin film interfaces (thickness less than 0.5 micrometers), and their multilayers deposited on engineering substrates. The present invention achieves separation and lift of thin film lines or their complete structures from semiconductor and engineering substrates using glass-modified stress waves. Apparatus and methods are further disclosed to catch these thin films or structures on desired substrates for reconstructing structures. This can lead to a faster way of fabricating MEMS and nano-scale devices by bypassing the currently used wet-etching techniques. This method can also provide an attractive alternative to create nanocircuitry or microcircuitry.

Figure 1:
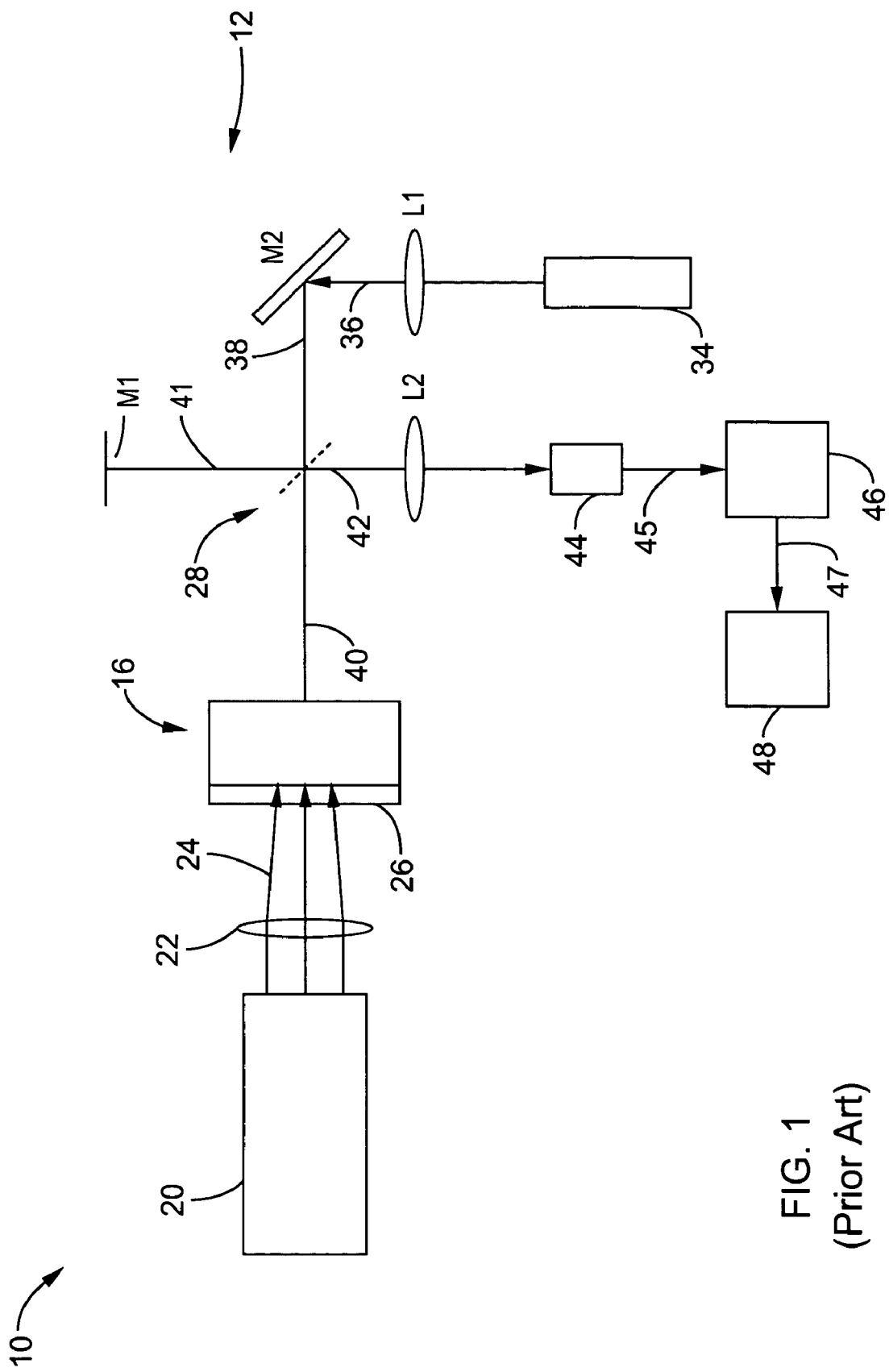
FIG. 1 is a schematic diagram of a laser spallation tensile strength measuring system using a laser Doppler displacement interferometer.

FIG. 1 illustrates an interface tensile strength measuring system using a laser Doppler displacement interferometer 12 and a laser spallation setup. An input laser 20 generates a pulse beam of light along a first axis. A first optical element 22 is positioned along the first axis to receive the input beam of light. The element 22 collimates the input beam and passes the collimated beam 24 along a second axis substantially parallel to the first axis and in line with sample assembly 16. Sample assembly 16 generally comprises a constraining element, an energy absorbing layer, a substrate element, and a sample coating, which are sequentially spaced along the second axis and disposed transverse thereto.

The laser Doppler displacement interferometer system 12 is a measuring means including a second input laser 34, a first collimating lens L1 positioned so as to receive the laser 34 input beam, and a first stationary mirror M2. The mirror M2 is angularly offset from the first collimating lens L1 to pass the laser beam along a first reflecting axis 38. The first reflecting axis 38 is substantially transverse to the input beam generated by the laser 34. A beamsplitter 28 is disposed along the reflecting axis 38 so as to receive a selected portion of the input beam 38. A portion of the beam incident upon the beamsplitter 28 passes therethrough a second reflected axis 40. Additionally, a selected portion of the beam that passes along the reflecting axis 38 is directed along a first output axis 41 to a second stationary mirror M1 by the beamsplitter 28. The laser beam that passes along the second reflecting axis 40 is incident upon the free surface of sample assembly 16, and is reflected back along the axis 40 to the beamsplitter 28. The beamsplitter 28 passes a selected portion of the beam reflected from the sample assembly 16 along the second output axis 42. The first and second output axes 41, 42 are disposed transverse to the reflecting axes 38, 40. A second collimating lens L2 is positioned along the second output axis 42 so as to receive the reflected portion of the beam from the beamsplitter 28. The second collimating lens L2 passes the beam along the second output axis 42 to a photodiode 44. The photodiode 44 is also positioned along the second output axis 42 to receive the reflected beam. The photodiode 44 generates a signal 45 in response to the reflected portion of the beam incident thereon. The photodiode signal 45 is in electrical communication with a digitizer 46. The digitizer 46 also generates an output signal 47 which is in electrical communication with a computer 48.

To measure the vibrations caused in the free surface of the sample assembly 16, the laser Doppler displacement system 12 of FIG. 1 is employed. The laser 34 is actuated to produce a laser beam along the axis 36. The first collimating lens L1 collimates the beam and passes the beam along to the stationary mirror M2. The mirror M2 is angularly offset with respect to the axis 36. The mirror M2 reflects the laser 34 beam along the reflecting axis 38. The beamsplitter 28 is positioned along the reflecting axis 38 so as to receive the reflected laser beam. The beamsplitter 28 passes a selected portion of the reflected beam along the reflecting axis 40, while simultaneously passing a selected portion of the incident beam along the first output axis 41. In the preferred embodiment, the beamsplitter can be disposed at any angle with respect to the reflecting axis 38, but is preferably at a 45 degree angle thereto. Moreover, the beamsplitter preferably divides the laser beam into two equal beams.

The beam which is reflected from the stationary mirror M1 is the reference beam and the beam reflected from the free surface of the coating 32 along the second axis 40 is the signal beam. The reference beam and the signal beam are intermixed at the beamsplitter 28, and are passed along the second output axis 42. The lens 22, preferably a convex lens, collimates the mixed beam and passes the beam along the axis 42 to the photodiode 42. The photodiode 44 produces a signal 45 that is proportional to the movement, e.g., transient velocity, of the coating free surface. The photodiode 44 output voltage signal is in electrical communication with the digitizer 46. The digitizer is then actuated to produce an output signal 47 that communicates with the computer 48.

The digitizer 46 produces a signal 47 corresponding to the fringe record of the photodiode 44. The fringe record is related to the velocity of the sample assembly free surface 16 by the computer 48. The transient velocity of the coating free surface is then related to the interface stress via a series of wave mechanics equations. More specifically, the peak interface tensile stress generated at each level of the laser fluence is related to the maximum free surface velocity via computer 48. Computer 48 takes the stress pulse measured at the substrate's free surface (measured separately) and impinges it upon the interface at the substrate side, and determines the resulting peak tensile amplitudes of the stress (which is normalized via a normalizing factor) at the interface and the coating free surface. The ratio of the foregoing amplitudes comprise the transfer coefficients which are then used to convert the measured peak stress at the coating or the substrate free surface to the interface peak stress.

Figures 2A, 2B:
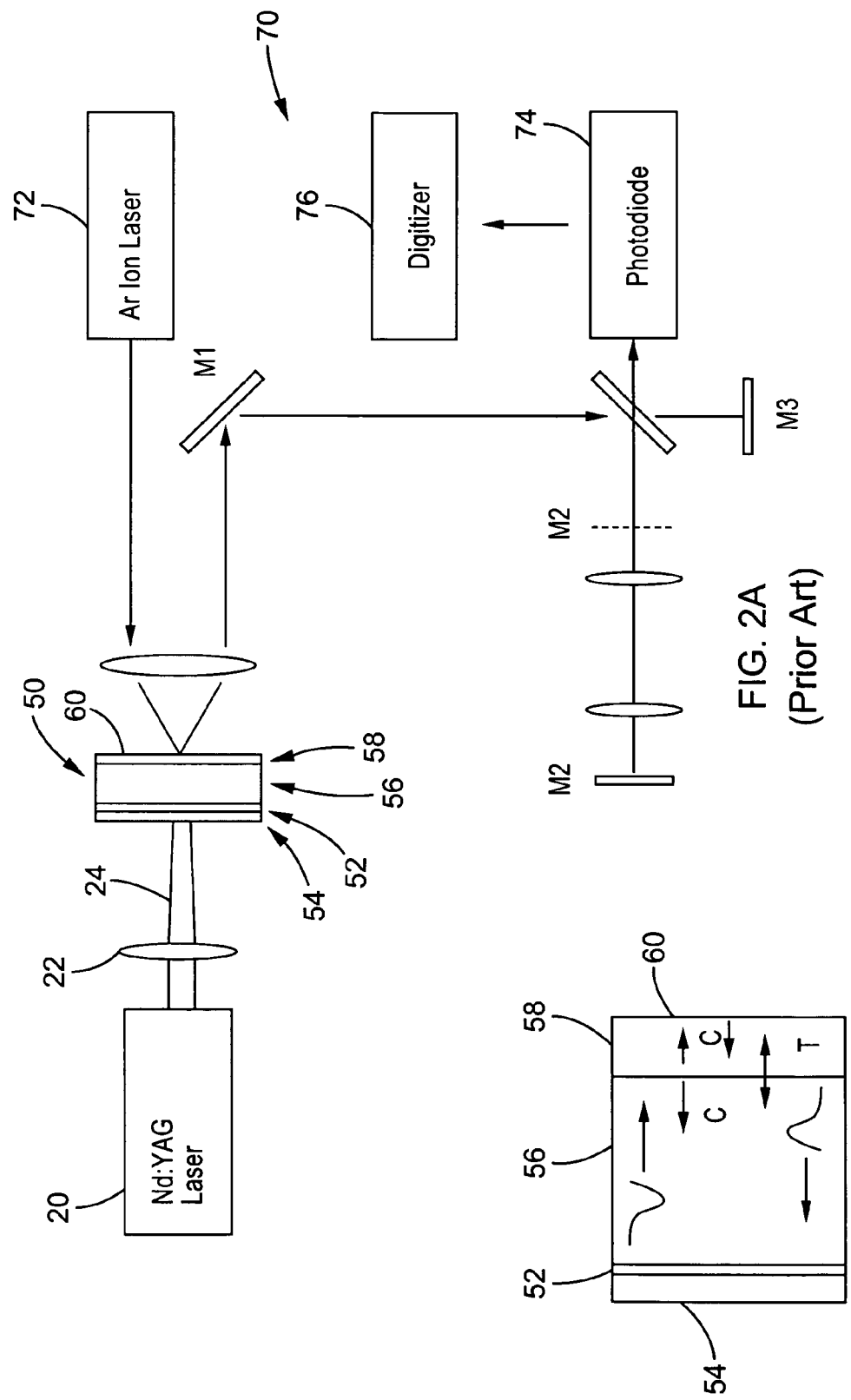
FIG. 2A shows a test setup for testing adhesion characteristics of prior art thin film samples.
FIG. 2B illustrates an expanded view of a cross-section of a prior art thin film sample assembly.

FIG. 2A illustrates an experiment using laser spallation techniques commonly used in the art. A 3-nanoseconds (ns) long Nd:YAG laser pulse was directed at sample assembly 50 and made to impinge over a 3 mm-dia area on a 0.5 μm thick aluminum film 52 that is sandwiched between the back surface of a substrate disc (having a 12-25 mm diameter and 1-mm thickness) and a 10 to 20 μm thick layer of $SiO_2$.

When actuated, the first input laser 20 generates a laser pulse that passes along the first axis to the lens 22. The lens 22 collimates the laser pulse into a collimated beam 24 that is incident upon a constraining layer 50.

The constraining material 50 is generally transparent to the input laser pulse, thereby transferring the pulse to the energy absorbing aluminum layer 52. Absorption of the laser pulse by the energy absorbing layer 52 leads to a sudden melting-induced expansion of the aluminum layer 52 which, due to the axial constraints of the assembly, e.g., the constraining material 54 and the substrate 56, generates a compressive shock wave or pulse directed towards the substrate 56 and the test coating 58, which is deposited on the substrate 56 front surface.

As illustrated in FIG. 2B, the compressive stress pulse propagating through the substrate 56 is incident upon the interface between the substrate 56 and the test coating or sample 58. A part of the compressive pulse is transmitted into the coating as the compression pulse strikes the interface. The compressive pulse reaches the coating free surface 60 where it is reflected, thereby forming a tension pulse T. The interface tensile stress is obtained by measuring the transient displacement history of the coating's free surface 60 (induced during pulse reflection) by using an optical interferometer 70 a schematic of which is shown FIG. 2A. It is this formation of the tension pulse T that leads to the removal of the coating 58 from the substrate/coating interface, given a sufficiently high amplitude.

When the stress pulse is reflected from the free surface 60 of the coating 58 or the substrate 56, the particles at the free surface experience a transient velocity, which is proportional to the transient profile of the striking stress pulse. This transient velocity is measured directly by the laser Doppler interferometer system 70 of FIG. 2A. Doppler interferometer system 70 comprises a second input (Ar Ion) laser 72, a series of collimating lenses, mirrors M1-M3, and a photodiode 74 and digitizer 76.

For a coating of density ρ and thickness h, the interface stress δ is calculated from the measured transient velocity v(t) as:

$$\delta(h,t) = \frac{1}{2} \rho c [v(t+h/c) - v(t-h/c)]$$

where c is the longitudinal stress wave velocity in the film.

Figure 3:
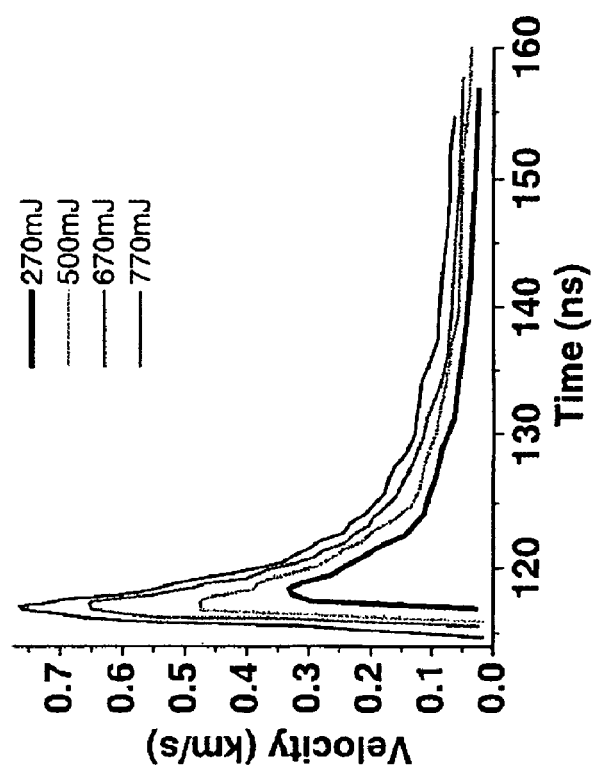
FIG. 3 illustrates measured stress pulse profiles in silicon at increasing laser fluence.

Laser-generated stress wave profiles that are used to decohere films in the basic technology discussed above are reproduced in FIG. 3. These measurements were made with a Si wafer substrate. The rise and post-peak decay time do not change significantly with increasing stress pulse amplitudes obtained at increasing laser fluences. A typical stress pulse profile has a rise-time of 1-2 ns, and a gradual post-peak decay of about 16-20 ns. However, stress waves up to several hundred nanoseconds can be generated in composite substrates. If the film is very thin compared to the length of the stress wave, then the tail end of the initial compression pulse is still at the interface while its front end has returned as a tensile wave after reflecting from the film's free surface. Because of destructive interference, the peak interfacial tensile stress is always less than the amplitude of the initial compression wave.

The amplitude of the peak interface tensile stress decreases non-linearly with the film thickness, the rise-time and post-peak decay time of the stress pulse, and becomes zero in the limiting case of zero film thickness. Thus, for thin layers, the peak interfacial tensile stress can be much lower than the peak tensile stress inside the substrate. For intrinsically strong interfaces, such a condition usually leads to failure within the substrate before the desired interface can be separated.

Table I summarizes interface tensile strength measurements using the basic laser spallation technique for a Cu/TaN bilayer system with the coating 58 sputter-deposited on the Si wafer substrate 56. Failure was observed inside the Si substrate 56 for the first three samples because of insufficient film thickness of coating 58. A consistency in the peak tensile stress inside the Si substrate for these samples was noted, indicating a tensile strength of Si of 5 GPa. For these samples the Si/TaN interface tensile stress is rather low, and below its interfacial strength. As the film thickness was increased, the failure locus changed from the substrate to the interface. Consistently, the peak tensile stress inside Si was lower than its strength measured in previous samples. The interface strength was found to be the same for the last two samples, indicating that if the interface chemistry is the same for films of varying thicknesses then the experiment measures the same fundamental strength. Thus, the interface strength can be measured in ultra thin film samples by simply increasing the film thickness or adding another layer on top to provide enough "room" for the reflecting compression pulse.

However, because of issues related to possible film structure and chemistry changes due to increased film thickness in several systems, the preferred way is always to test films in their initial low thickness state or in the same form as to be used in actual service devices and applications. Accordingly, successful spallation of ultra thin films (thickness less than 0.5 μm) and consequential and measurement their adhesion has become increasingly important.

Using a finite element-based simulation, Yuan and Gupta (1993) showed that for a given coating thickness the post-peak decay time is the most critical in maximizing the interfacial tensile stress. Indeed, if the post-peak decay time is reduced to zero, i.e. the wave profile has a "rarefaction shock," then the interface tensile stress for a film of arbitrarily small thickness theoretically will equal the amplitude of the incoming compression pulse. In accordance with the present invention, this theoretical possibility has been realized experimentally with sample assemblies using glass layers.

Figure 4:
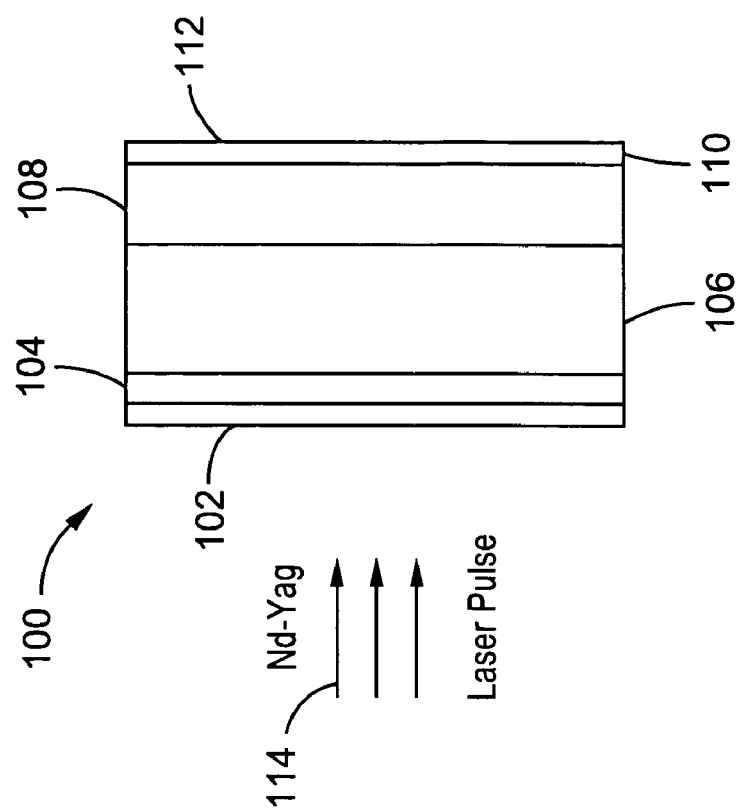
FIG. 4 is a cross-section view of an exemplary thin-film sample assembly in accordance with the present invention.

FIG. 4 illustrates an exemplary sample assembly 100 in accordance with the present invention. The sample assembly 100 comprises a constraining element 102, an energy absorbing layer 104, a glass substrate element 106, a silicon substrate element 108, and a coating 110 having a free surface 112, all sequentially spaced along an axis and disposed transverse thereto and in intimate facing contact.

As shown in FIG. 4, Nd-Yag laser pulse 114 is directed at the sample assembly 100 generally transverse to the constraining layer 102. The laser pulse passes through the water-glass constraining layer 102 to impinge and heat up energy-absorbing aluminum layer 104. Subsequent expansion of the aluminum layer 104 generates a compressive shock wave or pulse that propagates through the glass substrate 106 and silicon substrate 108. The pulse wave is transmitted into the coating 110 to form a tension pulse.

The energy absorbing layer 104 may be composed of a variety of metallic or non-metallic materials such as gold or germanium or even ordinary black scotch tape, but is preferably composed of a thin aluminum film. The constraining element 102 is preferably composed of solid water glass and is between 5 micrometers and 100 micrometers thick; and preferably 5 micrometers. The constraining element may also comprise a number of other compositions with similar qualities known in the art, such as 2-propanol, water, silicon dioxide. In alternative embodiments, the constraining element may even comprise transparent scotch tape.

The silicon substrate 30 is preferably circular in nature and is composed of a single crystal silicon (Si) wafer that is between 10 millimeters and 30 millimeters in diameter, and preferably, 1 millimeter thick. The sample coating 32 may be less than 0.5 micrometers thick.

The stress waves were measured with glass substrate elements 108 comprising Pyrex, soda lime, quartz, and borosilicate glasses using the experimental procedure that is embodied in FIG. 1 and U.S. Pat. No. 5,438,402, incorporated herein by reference in its entirety. To define the entering stress wave profile in the glass specimen accurately, these tests were performed by bonding the glass slides of nominal 1.0 mm thickness to 0.7 mm thick Si wafers using a 0.5 μm-thick optical grade EPOTECH 301 FL epoxy. The stress wave was generated inside the Si by exfoliating a waterglass-constrained Al film 104 in a manner discussed above. For interferometric measurements, a 400 Å layer of Al was deposited on the free surface of the glass.

Figure 5B:
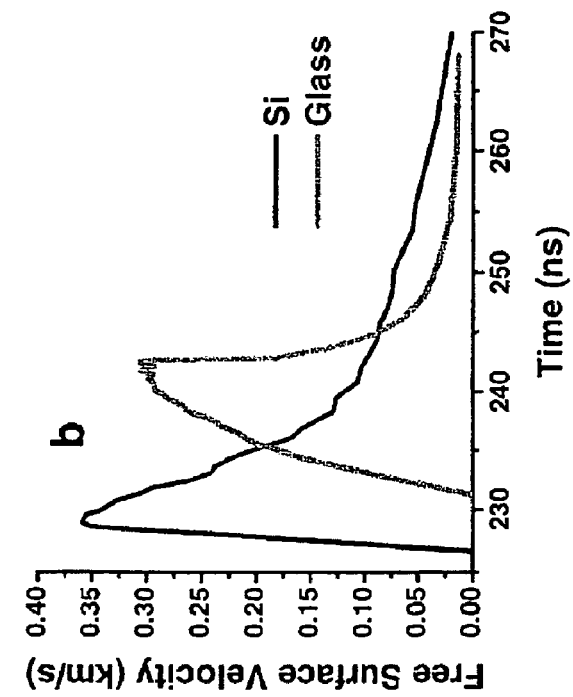
FIG. 5B shows a graph comparing the stress wave profile of soda lime glass with that of Si.
Figure 5A:
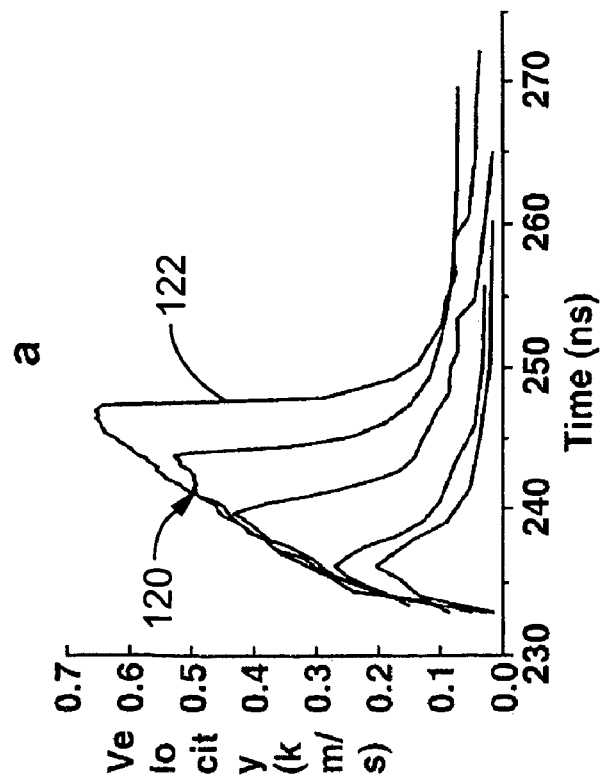
FIG. 5A shows a graph of stress wave profiles in soda lime glass under increasing laser fluence.

FIGS. 5A and 5B shows a series of stress pulse profiles with increasing laser fluence, measured with a glass substrate element 108 comprising soda lime glass. As illustrated in FIG. 5A, at low stress amplitudes, the profiles are similar to that in Si and other materials, having a finite rise-time and gradual post-peak decay. However, as the stress pulse amplitude exceeds a certain threshold, the rise-time of the stress wave 120 gets longer but the post-peak stress profile starts 122 to decay rather quickly. Ultimately, a profile is attained with the post-peak stress dropping virtually instantaneously (the drop time is within the resolution limit of our instrumentation), much like a "rarefaction shock." The modification in the stress wave profile as a result of the glass substrate element sample assembly 100 compared with a sample assembly having only a Si substrate is shown in FIG. 5B.

Figure 6:
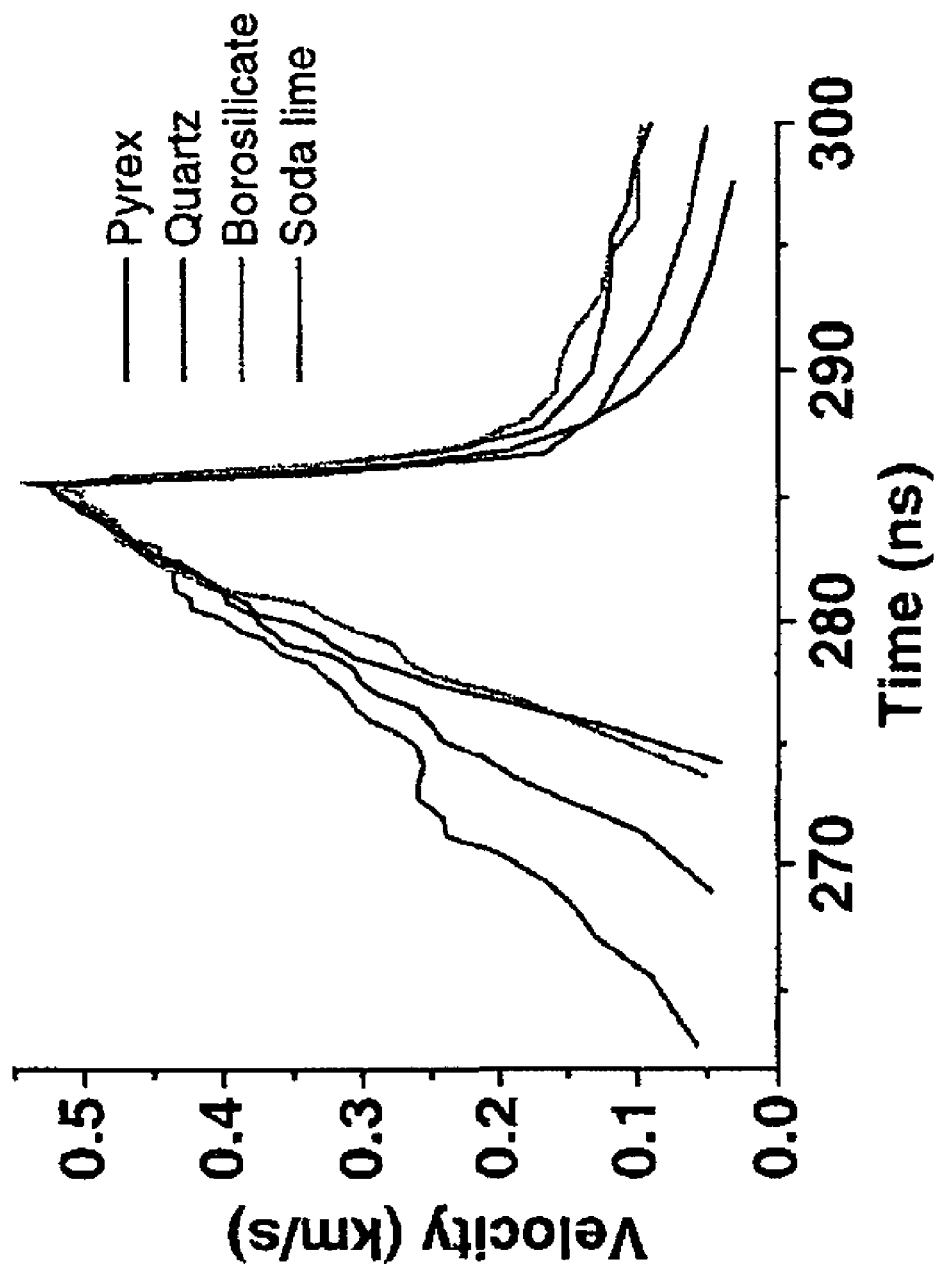
FIG. 6 shows a graph of stress wave profiles in different types of glass.

FIG. 6 shows the pulse profiles measured with Pyrex, soda lime, quartz, and borosilicate glasses as glass substrate elements 108. The magnitude of the above effect was found to vary from glass to glass, but all showed the formation of the rarefaction shock.

Previous investigators using plate impact setups were unable to uncover the formation of rarefaction shocks in glasses, since the pulse lengths in their work were larger than the specimen thickness. As suggested above, the rarefaction shock effect develops due to the finite propagation distance of the pulse into the material. This became possible in the setup of the present invention is able to achieve these results because of the short length (~0.1 mm) of the stress waves compared with the specimen thickness (~1 mm).

To demonstrate the use of glass-modified stress waves, the sample sets summarized in Table II were prepared. All films (coating 110) were sputter deposited onto the substrate, with thickness indicated in the table. The stress waves were directly generated inside the glass. Consistent with the laser spallation procedure, the free surface of the glass was coated with a 0.5 μm-thick Al film and constrained from top using a 40-50 μm-thick layer of water glass. The TiN/glass, and the Ni/glass systems, which have interest in display technology, were chosen to demonstrate the applicability of the glass-modified waves in decohering very thin film interfaces.

In addition to the glass substrates, a Cu(1400 nm)/TiN(70 nm) bilayer system was deposited as the coating 112 on the free surface of the Si substrate wafer 108. Previously, when the stress pulse was directly generated inside the Si wafer, failure within Si was observed, as shown in sample 1 in Table II. This, as discussed above, resulted because of the very high strength of the interface.

Figure 7B:
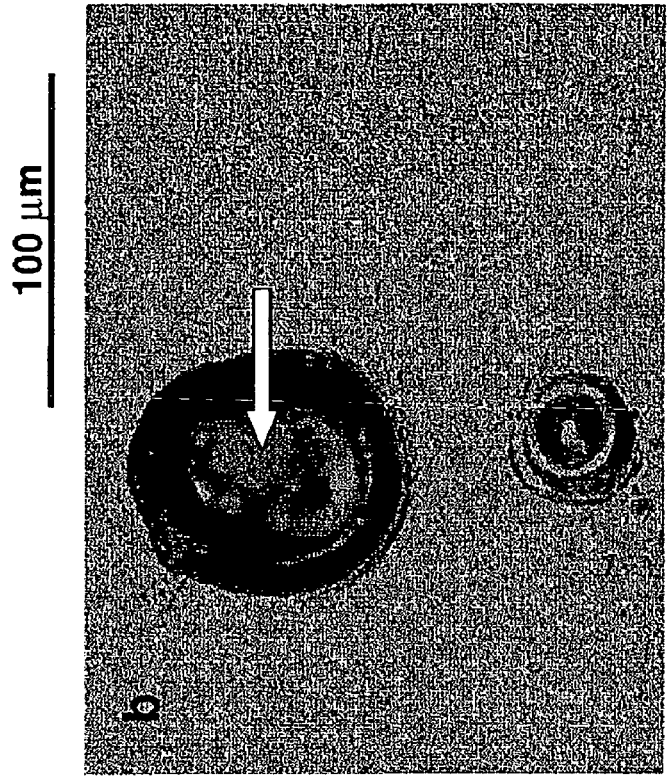
FIG. 7B is a photo depicting the failure locus in a Cu/TiN/Si system with glass.
Figure 7A:
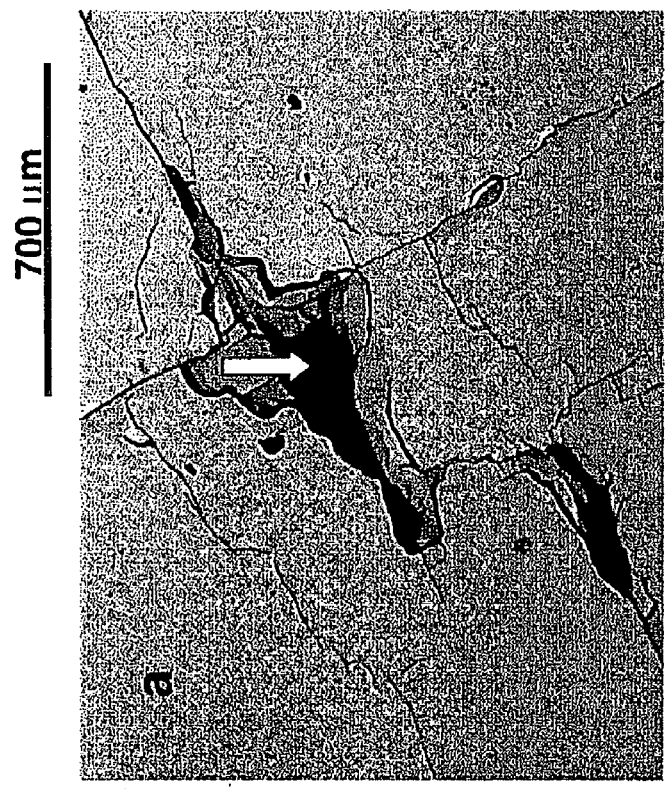
FIG. 7A is a photo depicting the failure locus in a Cu/TiN/Si system without glass.

In testing the present invention, the coating-free surface of the Si substrate 108 was bonded using an UV-cured epoxy to a Pyrex, quartz or borosilicate glass layer 106 to allow loading due to glass-modified waves. Consistent with the spallation procedure, laser-absorbing Al layer 104 was deposited on the backside of the glass substrate 106 and constrained by a 40-50 mm-thick layer of waterglass 102 from the top. Table II illustrates the failures observed at the interfaces of interest for the various configurations, with specific tensile strength values for each configuration. Table II demonstrates the potential of using glass substrates in accordance with the present invention in measuring the tensile strength of very thin film interfaces. FIGS. 7A and 7B illustrate the contrasting failure locus realized between sample #1 and sample #2 of Table II. As shown in FIG. 7A, the failure locus occurred inside the Si substrate 108 in the Cu(1400 nm)/TiN(70 nm)/Si system when no glass substrate was used. In contrast, FIG. 7B shows a high magnification view of failure when the glass-modified waves of the present invention were used. The arrow shows the failure to be at the Cu/TiN interface (i.e. within the coating layer 110) with no fracture inside the Si substrate 108. An interface tensile strength value of 2.62 GPa was calculated. This is a rather high value, which was not possible to attain using the basic spallation setup.

Figure 8B:
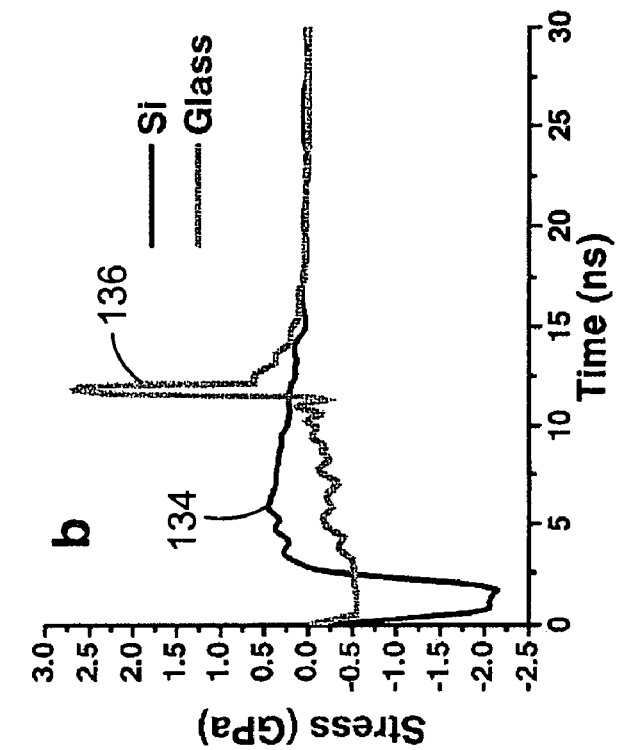
FIG. 8b shows a graph comparing the stress history at the Cu/TiN interface of the systems of FIG. 7A and 7B.
Figure 8A:
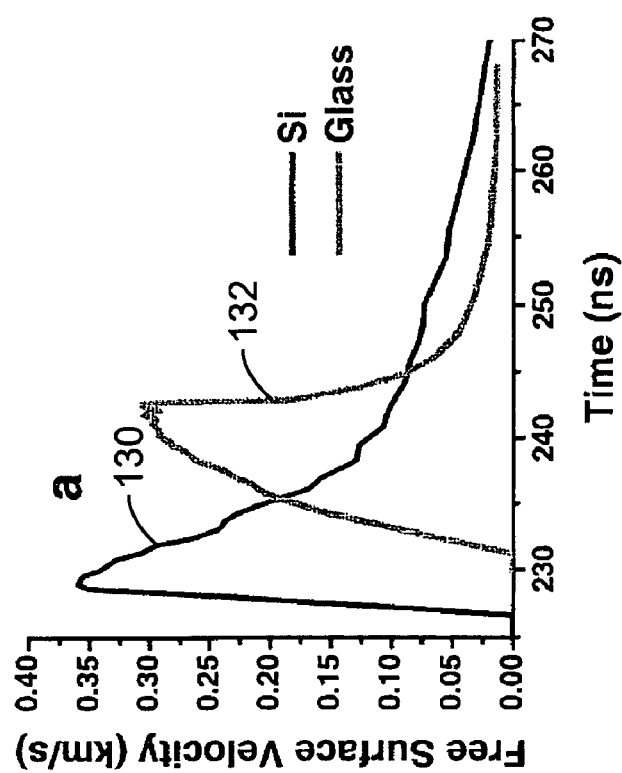
FIG. 8A shows a graph comparing the surface velocity profiles of the systems of FIG. 7A and 7B.

The results shown in FIGS. 7A and 7B are quantitatively shown in FIGS. 8A and 8B. FIG. 8A shows the measured free surface velocity profiles 130 and 132 achieved from the borosilicate glass modified waves and Si substrate generated waves corresponding to the failures shown in FIGS. 7A and 7B. Accordingly, rarefaction shock behavior was observed in the borosilicate glass modified wave generated profile 132. The interface tensile stress history 134 and 136 corresponding to the borosilicate glass modified wave profile and is substrate profile is shown in FIG. 8B. As can be seen in FIG. 8B, a dramatic increase in the interface tensile stress profile 136 was observed in the glass-modified wave.

A related application that could become significant in the nanotechnology area is the use of these special waves in MEMS and nanoelectronics device fabrication such as manufacturing nanoscale circuits and devices having structures composed of nanowires on electronic substrates (Si, Ge, etc.). Nanocircuitry-based devices are expected to lead to significantly faster processing speeds than those possible with the current micron-scale-technology. The photolithography technology used today has essentially reached its limit in terms of the smallest feature size that can be manufactured. New ideas for nanowire fabrication include, E-beam etching (which is extremely slow), and anisotropic-lattice-mismatch-based film deposition ideas. In the latter approach, the materials for the film and the substrate are chosen such that there is a substantial lattice mismatch in one direction, and almost none in another. The large mismatch constrains film growth, while encouraging film growth in the zero-lattice-mismatch-direction. This procedure is thus constrained to few selected film/substrate combinations.

Figure 9A:
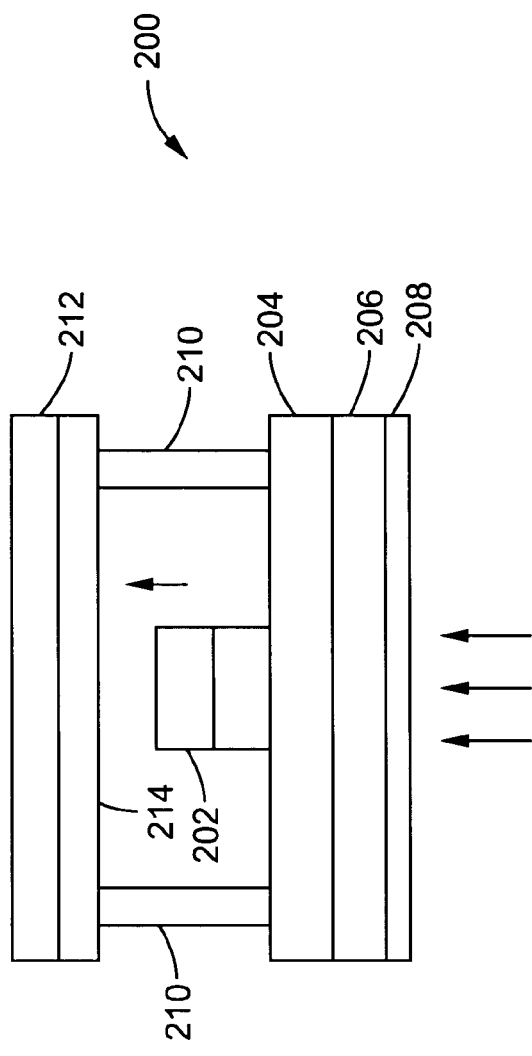
FIGS. 9A and 9B illustrate a schematic of a nanowire separation and retrieval assembly 200 in accordance with the present invention
Figure 9B:
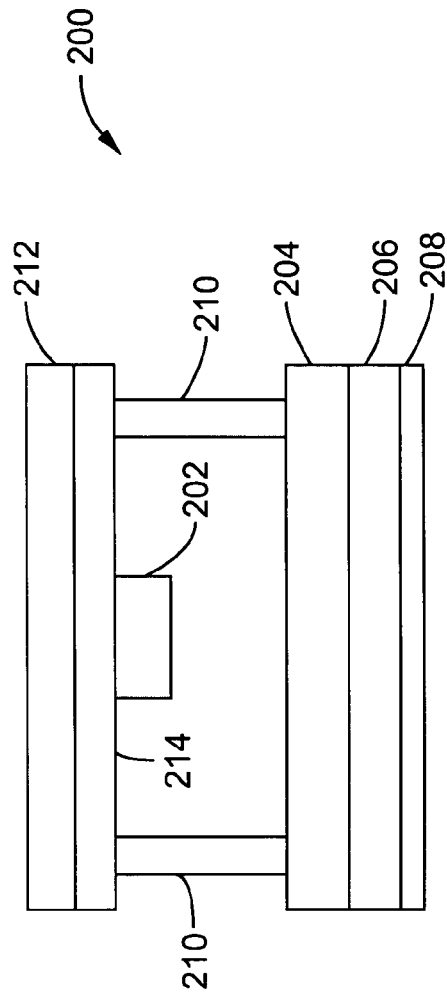

FIGS. 9A and 9B illustrate a schematic of a nanowire separation and retrieval assembly 200 in accordance with the present invention. Nanowire 202, which is deposed on specialized substrate 204 for synthesizing nanowire growth, may be separated using the principles of the present invention. As discussed above in FIG. 4, a laser pulse may be directed at the thin Al layer 208 on the free side of the glass substrate 206, causing compression shock waves to propagate through the glass substrate 206 and adjacent silicon substrate 204. The shock waves reflect off of nanowire 202 to generate a tensile force that separates the nanowire 202 from the silicon substrate 204. As discussed above, separation of such thin wires is only possible using the glass-modified waves of the present invention.

As illustrated in FIG. 9B, the separated wires may then be then "caught" or retrieved on a desired electronic substrate 212 located opposite the free surface of the nanowire 202 and separated thereby via spacers 210. The electronic substrate 212 may have either a very thin layer of adhesive 214 or a self-assembled molecular layer. Circuits can then be constructed by repeated use of this procedure. Under this configuration, there are no restrictions on the type of substrate used.

Figures 10A, 10B:
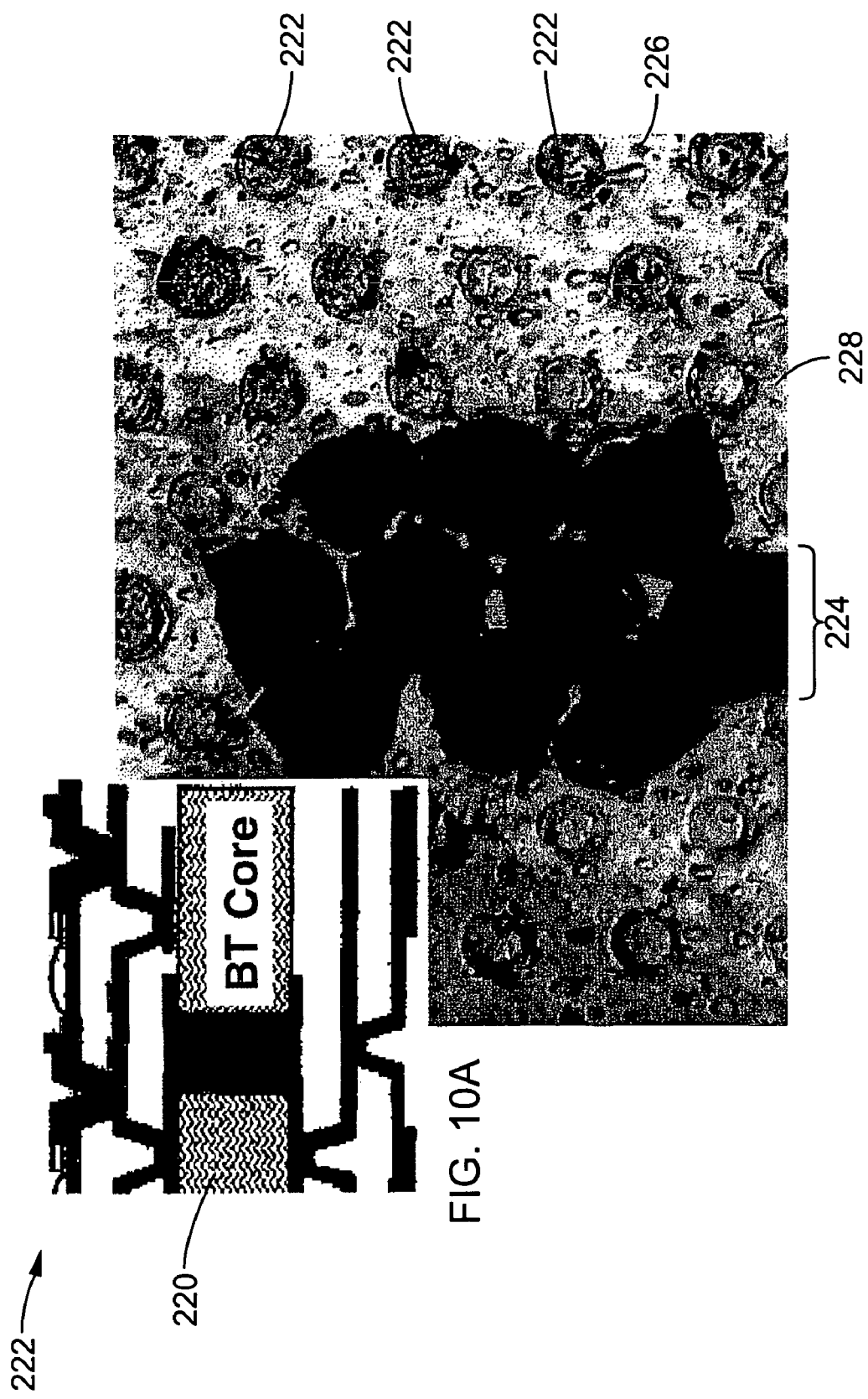
FIG. 10A is a cross sectional view of a multi-layer plastic substrate having lead bumps in accordance with the present invention.
FIG. 10B is a photo illustrating the stress wave separated lead bumps caught on a flexible plastic tape in accordance with the present invention.

Physical illustration of the system of FIG. 9A is demonstrated on a multilayer plastic substrate 220 having a cross-section as shown in the FIG. 10A. The view of FIG. 10B of the top layer shows lead bumps 222 that are used for electrical contacts allowing the Si device to communicate with the substrate circuitry. A laser was impinged onto the undersurface of the plastic substrate 220 in accordance with the present invention to launch the stress wave towards the top layer of the substrate. The stress wave separated the lead bumps 222 and these separated bumps were caught on a flexible plastic tape 226 as shown in FIG. 10B.

Figure 11:
FIG. 11 shows a focused view of the separated lead bumps in their entirety.

The success of this procedure is demonstrated in FIG. 10B and FIG. 11, which shows low and high magnification micrographs of the separated lead bumps 222 on the tape 226. It was additionally noted that as the laser energy was increased, separation below the lead bump areas was also accomplished.

Thus, in such cases, the lead bumps 222 along with their underlying film were pulled free from the substrate 220 and caught on the plastic tape 226. The dark region 224 in FIG. 10A is the layer that was below the bumps, which now appears on the very top of the flexible tape substrate 226. FIG. 11 shows a focused view of the separated lead bumps in their entirety. Yet another application of the glass-modified waves is to make high performance circuits on flexible substrates such as plastics, e.g. for applications in manufacturing of low cost RFID tags, TFT-based high performance computers, and sensor systems.

Figure 12:
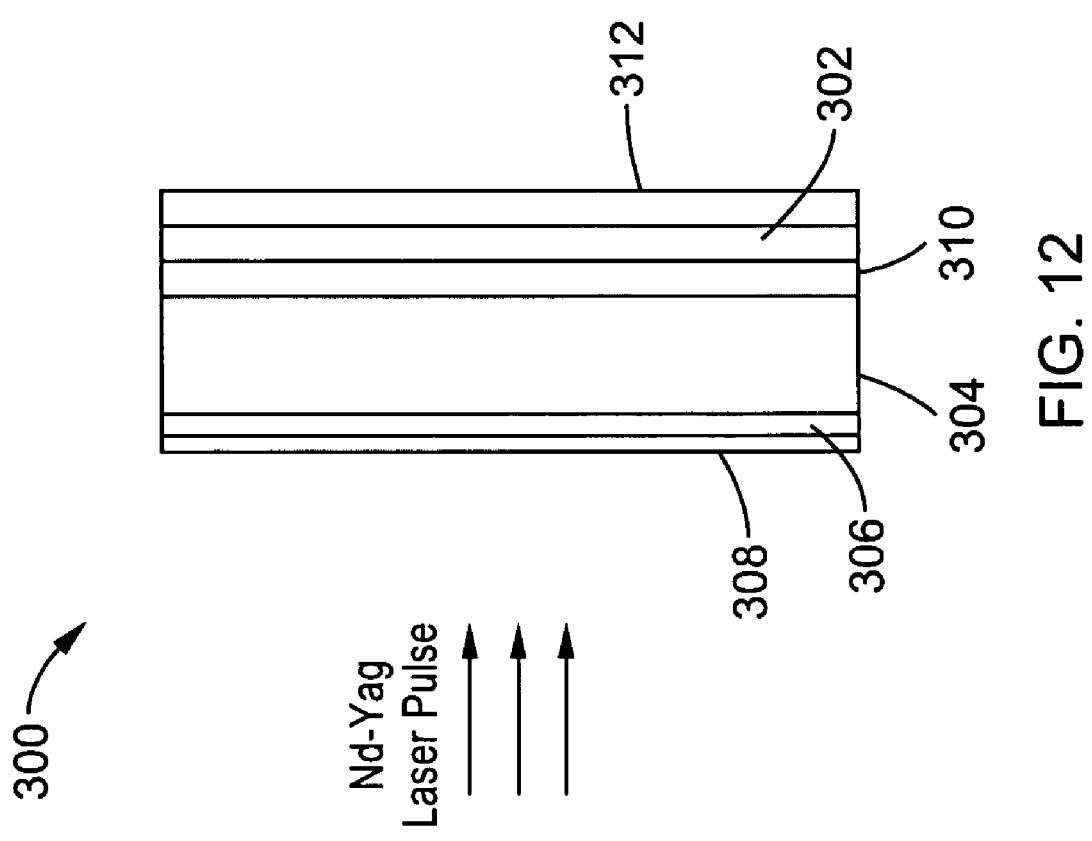
FIG. 12 illustrates an alternative embodiment of the present invention with a polysilicon surface spun coated with a polymer film.

As shown in FIG. 12, a very high quality polysilicon or a single crystal Si layer 302 may be positioned (over a finite area) on a glass or a quartz substrate 304 using already well-established process variables as described above. The glass substrate 304 may have a silica layer 310 optionally disposed between the silicon layer 302 and the glass substrate 304 on one side, with the aluminum film 306 and waterglass constraining element 308 on the free side of the glass substrate 304.

Already fabricated high performance circuits can be generated first on the Si or a glass platform 304. Next, the entire polysilicon surface 302 may be spun coated with the polymer film, i.e., the "recipient substrate" 312. This results in a glass/Si/polymer sandwich.

Figure 13:
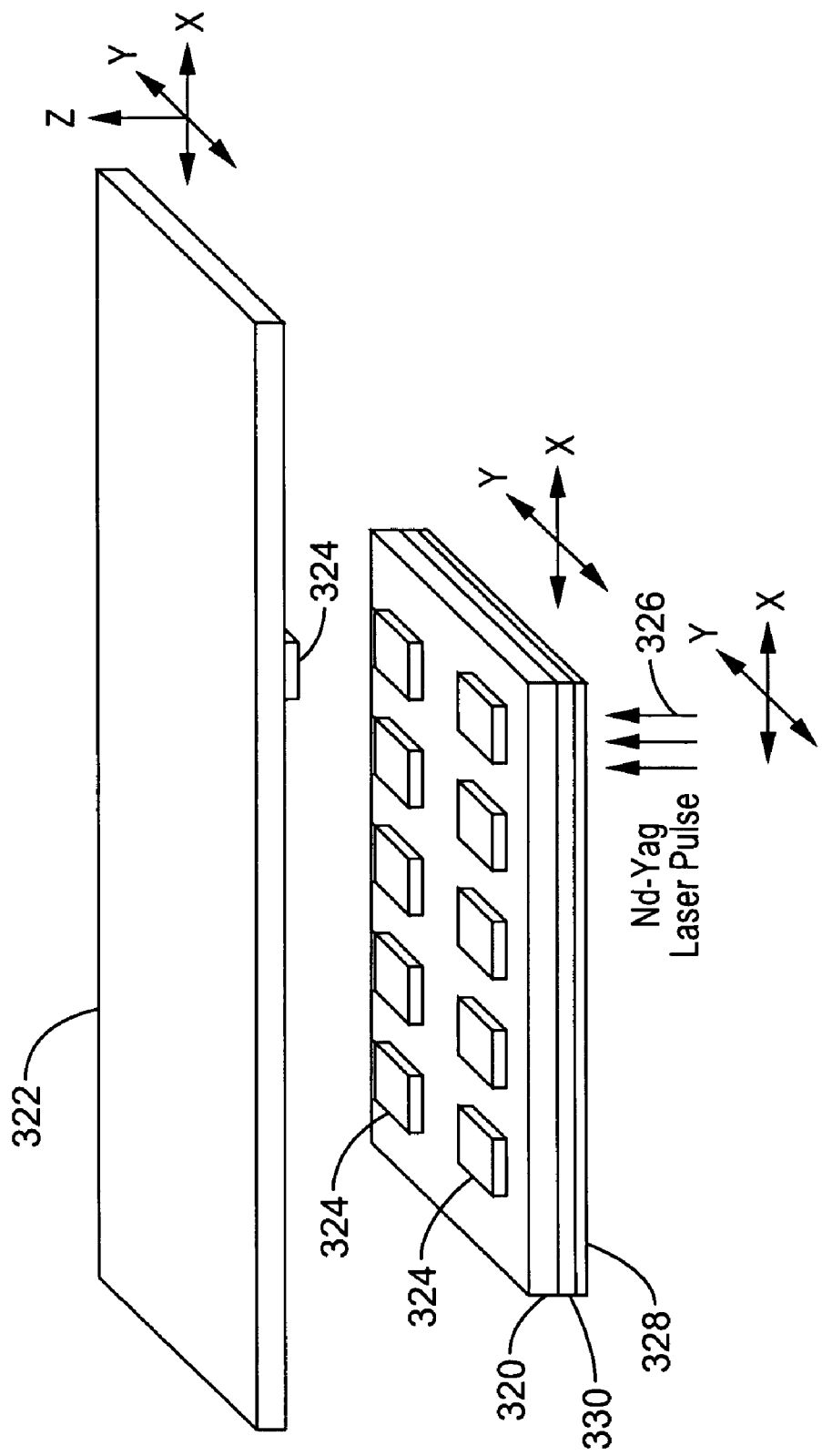
FIG. 13 illustrates another embodiment of the invention using a polymer foil.

Instead of spin coating the polymer substrate, an already formed polymer foil 322 could also be placed in closed vicinity of the Si platform 324 (which may comprise one or more circuits), as shown in FIG. 13. A high amplitude compressive stress wave will be generated on the backside of the glass substrate 320 by focusing a Nd:YAG laser pulse 326 onto a 0.5 mm-4 mm-dia area that has a water-glass (328)-constrained Al film 330. The stress wave will directly detach the Si/glass interface to completely transfer the entire Si film, Si platforms, or circuits 324 onto the plastic substrate.

In yet another embodiment, the Al layer 330 or the constraining waterglass layer 328 on the backside of the substrate 320 may be removed. In this configuration, the laser pulse 326 will go through the glass and directly interact with the Si surface to launch a stress wave. This wave will then pry off the Si/glass interface to transfer the Si platform 324 to the polymer substrate 322 on top. Thus, the mechanism of pattern transfer remains the same in both approaches.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE I

Effect of Film Thickness on the Failure Mode

| Configuration | Peak Interface Tensile Stress (MPa) | Peak Tensile Stress in the Substrate (MPa) | Failure Locus |
|---|---|---|---|
| Cu[100 nm]/TaN[20 nm]/Si | 38 ± 4 | 5100 | Si Failure |
| Cu[500 nm]/TaN[20 nm]/Si | 260 ± 18 | 4900 | Si Failure |
| Cu[1 μm]/TaN[20 nm]/Si | 280 ± 29 | 5200 | Si Failure |
| Cu[5 μm]/TaN[20 nm]/Si | 1380 ± 110 | 4700 | Interface Failure |
| Cu[10 μm]/TaN[20 nm]/Si | 1370 ± 140 | 4200 | Interface Failure |

TABLE II

Interface Tensile Strengths Measured Using Glass-Modified Stress Waves.

| Sample No. | Multilayer Configuration | Peak Interface Tensile Stress (MPa) | Peak Tensile Stress in Substrate (MPa) | Failure Locus |
|---|---|---|---|---|
| 1. | Cu(1400 nm)/TiN(70 nm)/Si | 451 | 5340 | Silicon failure |
| 2. | Cu (1400 nm)/TiN(70 nm/Si Borosilicate glass | 2620 ± 2120 | | Cu/TiN interface |
| 3. | Mo[400 nm]/Borosilicate glass | 577 ± 47 | 2624 | Mo/Borosilicate glass interface |
| 4. | Mo[1000 nm]/Borosilicate glass | 245 ± 26 | 1050 | Borosilicate glass Failure |
| 5. | Mo[400 nm]/Borosilicate glass | 577 ± 33 | 2624 | Mo/Borosilicate glass interface |
| 6. | Mo[400 nm]/Pyrex | 135 ± 11 | 1125 | Mo/Pyrex interface |
| 7. | Mo[400 nm]/Quartz | 99 ± 8 | 1110 | Mo/Quartz interface |
| 8. | Mo[1000 nm]/Borosilicate glass | 233 ± 24 | 980 | Borosilicate glass failure |
| 9. | Mo[1000 nm]/Pyrex | 53 ± 6 | 470 | Borosilicate glass failure |
| 10. | Mo[1000 nm]/Quartz | 48 ± 4 | 460 | Borosilicate glass failure |
| 11. | TiN[320 nm]/Borosilicate Glass | 164 ± 11 | | TiM/Borosilicate glass interface |
| 12. | Ni[350 nm]/Borosilicate Glass | 120 ± 13 | | Ni/Borosilicate glass interface |
| 13. | Cr[400 nm]/Borosilicate glass | 197 ± 16 | 2100 | Cr/Borosilicate glass interface |
| 14. | Mo[1000 nm]/Cr[400 nm]/Borosilicate glass | 210 ± 19 | 980 | Cr/Borosilicate glass interface |

What is claimed is:

1. An apparatus for generating a tensile stress between a substrate and a coating, comprising:
   a substrate having a thickness, said thickness defined by a first side and a second side in a first axis;
   a coating applied to the first side of the substrate such that the coating and substrate are axially spaced along the first axis in intimate facing contact with each other such to form a coating/substrate interface; and
   a glass element disposed on the second side of the substrate and axially spaced along the first axis;
   wherein the glass element is configured to propagate and modify a stress wave to the coating/substrate interface to generate a tensile stress between the substrate and the coating.

2. An apparatus as recited in claim 1, wherein the tensile stress is configured to separate the coating from the substrate at the coating/substrate interface.

3. An apparatus as recited in claim 1, wherein the glass is configured to propagate the stress wave as a result of impingement by a Nd-Yag laser beam directed in the first axis.

4. An apparatus as recited in claim 1, wherein the stress wave has a length ranging from approximately 5 nanoseconds to approximately 1 microsecond.

5. An apparatus as recited in claim 4, wherein the stress wave comprises a rarefaction shock formation.

6. An apparatus as recited in claim 1, wherein the coating has a thickness less than approximately 0.5 μm.

7. An apparatus as recited in claim 1, wherein the glass element is bonded to the second side of the substrate.

8. An apparatus as recited in claim 1, wherein the glass element comprises one of the following: Pyrex, soda lime, quartz, or borosilicate.

9. An apparatus as recited in claim 1, wherein the glass element has a thickness ranging from approximately 0.1 mm to approximately 5 mm.

10. An apparatus as recited in claim 1, wherein the substrate comprises silicon.

11. An apparatus as recited in claim 1, further comprising a constraining element disposed adjacent to the glass element.

12. An apparatus as recited in claim 11, further comprising an energy absorbing layer disposed between the constraining layer and the glass element.

13. A method for separating a coating from a substrate, the substrate having a first side and a second side transversely disposed in a first axis, the coating applied to the first side of the substrate such that the coating and substrate are axially spaced along the first axis in intimate facing contact to form a coating/substrate interface, the method comprising:
   positioning a glass element along the first axis on the second side of the substrate;
   directing a laser pulse in the first axis at the glass element;
   propagating and modifying a stress wave through the glass element to the coating/substrate interface to generate a tensile force between the substrate and the coating; and
   separating the coating from the substrate as a result of the stress wave-generated tensile force.

14. A method as recited in claim 13, wherein directing a laser pulse in the first axis comprises directing a Nd-Yag laser beam in the first axis.

15. A method as recited in claim 13, wherein propagating a stress wave comprises propagating a stress wave having a length ranging from approximately 5 nanoseconds to approximately 1 microsecond.

16. A method as recited in claim 15, wherein the stress wave comprises a rarefaction shock formation.

17. A method as recited in claim 15, wherein the stress wave is configured to separate a coating having a thickness less than approximately 0.5 µm.

18. A method as recited in claim 15, wherein positioning a glass element along the first axis comprises bonding the glass element to the second side of the substrate.

19. A method as recited in claim 13, wherein the glass element comprises one of the following: Pyrex, soda lime, quartz, or borosilicate.

20. A method as recited in claim 19, wherein the glass element has a thickness ranging from approximately 0.1 mm to approximately 5 mm.

21. A method as recited in claim 13, further comprising positioning a constraining element adjacent to a free side of the glass element.

22. A method as recited in claim 21, further comprising:
coating an energy absorbing layer on the free side of the glass element between the constraining layer and the glass element;
wherein directing a laser pulse in the first axis comprises directing the laser pulse the energy absorbing layer coated on the glass element.

23. A method as recited in claim 13, wherein the stress generated by the stress wave at the coating/substrate interface exceeds approximately 1.0 GPa.

24. A method as recited in claim 23, wherein the stress generated by the stress wave at the coating/substrate interface exceeds approximately 2.0 GPa.

25. An apparatus for separating a nanostructure from a first substrate, the nanostructure attached to a front side of the first substrate, comprising:
a glass element disposed on a back side of the first substrate opposite the nanostructure; and
a laser source configured to direct a laser beam at the glass element;
wherein the glass element is configured to propagate and modify a stress wave to the nanostructure as a result of impingement by the laser beam to generate a tensile stress between the nanostructure and the first substrate to separate the nanostructure from the first substrate.

26. An apparatus as recited in claim 25, wherein the laser source comprises a Nd-Yag laser.

27. An apparatus as recited in claim 25, wherein the glass element comprises one of the following: Pyrex, soda lime, quartz, or borosilicate.

28. An apparatus as recited in claim 25, further comprising an energy absorbing layer disposed between the constraining layer and the glass element.

29. An apparatus as recited in claim 25, further comprising:
a second substrate located opposite the front side of the first substrate;
wherein the second substrate is configured to receive the nanostructure once separated from the first substrate.

30. An apparatus as recited in claim 29, further comprising:
an adhesive layer disposed on the second substrate;
wherein the adhesive layer is configured to form a bond between the nanostructure and the second substrate.

31. An apparatus as recited in claim 29, further comprising one or more spacers separating the first substrate from the second substrate.

32. An apparatus for transferring a silicon platform to a receiving substrate, comprising:
a glass substrate disposed on a back side of the silicon platform;
a laser source configured to direct a laser beam at the glass element;
wherein the glass element is configured to generate a tensile stress between the silicon platform and the glass substrate as a result of impingement by the laser beam; and
wherein said tensile stress is configured to launch the silicon platform to the receiving substrate; and
an energy absorbing layer adjacent the glass substrate opposite from the silicon platform;
wherein the energy absorbing layer and the glass substrate are configured to propagate and modify a stress wave across the glass substrate to generate the tensile stress between the silicon platform and the glass substrate.

33. An apparatus as recited in claim 32, wherein the laser beam passes through the glass substrate to generate the tensile stress between the silicon platform and the glass substrate.

34. An apparatus as recited in claim 32, wherein the silicon platform comprises one or more circuits.

35. An apparatus as recited in claim 32, wherein the receiving substrate comprises a polymer.

36. An apparatus as recited in claim 35, wherein the receiving substrate is spun coated with a polymer film.

* * * * *

(12) INTER PARTES REVIEW CERTIFICATE (4228th)

United States Patent
Gupta et al.

(10) Number: US 7,487,684 K1
(45) Certificate Issued: Dec. 22, 2025

(54) GLASS-MODIFIED STRESS WAVES FOR SEPARATION OF ULTRA THIN FILMS AND NANOELECTRONICS DEVICE FABRICATION

(75) Inventors: Vijay Gupta; Vassili A. Kireev

(73) Assignee: THE REGENTS OF THE UNIVERSITY OF CALIFORNIA

Trial Number:

IPR2024-00761 filed Apr. 1, 2024

Inter Partes Review Certificate for:

Patent No.: 7,487,684
Issued: Feb. 10, 2009
Appl. No.: 11/504,981
Filed: Aug. 15, 2006

The results of IPR2024-00761 are reflected in this inter partes review certificate under 35 U.S.C. 318(b).

INTER PARTES REVIEW CERTIFICATE
U.S. Patent 7,487,684 K1
Trial No. IPR2024-00761
Certificate Issued Dec. 22, 2025

AS A RESULT OF THE INTER PARTES REVIEW PROCEEDING, IT HAS BEEN DETERMINED THAT:

Claims 1-24 are found patentable.

\* \* \* \* \*